United States Patent
Jhong et al.

(10) Patent No.: US 12,086,983 B2
(45) Date of Patent: Sep. 10, 2024

(54) INTELLIGENT DANDRUFF DETECTION SYSTEM AND METHOD

(71) Applicant: MacroHI Co., Ltd., New Taipei (TW)

(72) Inventors: Sin-Ye Jhong, New Taipei (TW); Chih-Hsien Hsia, Taipei (TW)

(73) Assignee: MacroHI Co., Ltd., New Taipei (TW)

( * ) Notice: Subject to any disclaimer, the term of this patent is extended or adjusted under 35 U.S.C. 154(b) by 352 days.

(21) Appl. No.: 17/680,345

(22) Filed: Feb. 25, 2022

(65) Prior Publication Data
US 2023/0081592 A1 Mar. 16, 2023

(30) Foreign Application Priority Data
Sep. 13, 2021 (TW) ................................. 110134090

(51) Int. Cl.
G06T 7/00 (2017.01)
G06F 18/24 (2023.01)
G06N 3/045 (2023.01)

(52) U.S. Cl.
CPC ............ *G06T 7/0012* (2013.01); *G06F 18/24* (2023.01); *G06N 3/045* (2023.01); *G06T 2207/10056* (2013.01); *G06T 2207/30088* (2013.01)

(58) Field of Classification Search
CPC ......... G06T 7/0012; G06T 2207/10056; G06T 2207/30088; G06F 18/24; G06N 3/045; G16H 50/30
USPC ........................................................ 382/128
See application file for complete search history.

(56) References Cited

U.S. PATENT DOCUMENTS 8,809,014 B2 * 8/2014 Kosaga .................. A45D 44/00
424/9.8

FOREIGN PATENT DOCUMENTS

| CN | 110298393 A | 10/2019 |
| CN | 112084965 A | 12/2020 |
| CN | 113191953 A | 7/2021 |
| TW | 201914524 A | 4/2019 |

(Continued)

OTHER PUBLICATIONS

Vaswani, "Attention Is All You Need", arXiv, 2017 (Year: 2017).*

(Continued)

*Primary Examiner* — Juan A Torres
(74) *Attorney, Agent, or Firm* — Bruce Stone LLP; Joseph A. Bruce (57) ABSTRACT

A smart dandruff analysis system and method are provided for analyzing a severity of a subject's dandruff, and the smart dandruff analysis system has operation module, first neural network module, second neural network module, and classification module. The operation module receives a scalp area image of the subject and transforms the scalp area image into a first feature map. The first neural network module, a Convolutional Neural Network model, electrically connects with the operation module for receiving and transforming the scalp area image into a second feature map. The second neural network module, a Transformer model, electrically connecting with the first neural network module for receiving and transforming the second feature map into a third feature map. The classification module electrically connects with the second neural network module for receiving the third feature map and outputting a rating, wherein the rating is to determine the severity of the subject's dandruff.

7 Claims, 8 Drawing Sheets

(56) References Cited

FOREIGN PATENT DOCUMENTS

TW          I670042        9/2019

OTHER PUBLICATIONS

Brock, "High-Performance Large-Scale Image Recognition Without Normalization" arXiv, Feb. 2021. (Year: 2021).*
European search opinion (5 pages) for EP4148747 dated Jul. 14, 2022 (Year: 2022).*
Amendments received before examination (4 pages) for EP4148747 dated Aug. 31, 2023 (Year: 2023).*
Amended claims filed after receipt of (European) search report (3 pages) dated Aug. 31, 2023 (Year: 2023).*
Dosovitskly. "An image is worth 16×16 words: transformers for image recognition at scale" arXiv Jun. 2021. (Year: 2021).*
Sohn, "FixMatch: Simplifying Semi-Supervised Learning with Consistency and Confidence" 2020 (Year: 2020).*
Bacon, "Assessing therapeutic effectiveness of scalp treatments for dandruff and seborrheic dermatitis, part 1: a reliable and relevant method based on the adherent scalp flaking score (ASFS)" 2014 (Year: 2014).*
Chang et al., "ScalpEye: A Deep Learning-Based Scalp Hair Inspection and Diagnosis System for Scalp Health", IEEE, Jul. 21, 2020, pp. 134826-134837.

* cited by examiner

INTELLIGENT DANDRUFF DETECTION SYSTEM AND METHOD

BACKGROUND OF THE INVENTION

1. Field of the Invention

The present invention is in related to a dandruff analysis system and a method thereof, more particularly to a smart dandruff analysis system and a method thereof.

2. Description of the Prior Art

Dandruff is a problem that almost everyone has encountered. Some people with mild dandruff are able to purchase anti-dandruff shampoos on the market in order to solve the problem; but for other people with more serious dandruff conditions, seeking professional assistance may be necessary. However, those relative operators need a period of time for professional training, so as to be qualified to determine the conditions of dandruff, and it does rise up cost.

As it can be seen, how to solve aforesaid shortcomings, quickly analyzing a severity of a subject's dandruff with low cost, becomes an important issue to persons who are skilled in the art.

SUMMARY OF THE INVENTION

The present invention is to provide a smart dandruff analysis system and a method thereof. The present invention is able to automatically detect a severity of a subject's dandruff, so as to decrease a labor cost.

The smart dandruff analysis system is for analyzing a severity of a subject's dandruff, and has an operation module, a first neural network module, a second neural network module, and a classification module. The operation module receives a scalp area image of the subject and transforms the scalp area image into a first feature map. The first neural network module, a Convolutional Neural Network (CNN) model, electrically connects with the operation module in order to receive the scalp area image and transform the scalp area image into a second feature map. The second neural network module, a Transformer model, electrically connecting with the first neural network module in order to receive the second feature map and transform the second feature map into a third feature map. The classification module electrically connects with the second neural network module in order to receive the third feature map and output a rating, wherein the rating is to determine the severity of the subject's dandruff.

Preferably, the smart dandruff analysis system further has a scalp tester, which takes an area of a scalp of the subject to form the scalp area image, wherein the scalp tester is a digital microscope.

Preferably, the smart dandruff analysis system adopts a Semi-supervised Learning when training.

Preferably, the smart dandruff analysis system further has a compression module, which is connected between the first neural network module and the second neural network module, and receives and compresses the second feature map, then transmits the compressed second feature map to the second neural network module.

Preferably, the operation module is disposed on at least one terminal device, and the first neural network module, the second neural network module and the classification module are disposed on at least one server.

The method for analyzing a severity of a subject's dandruff comprising the steps of: acquiring at least one scalp area image of the subject, and transforming the scalp area image into a first feature map; inputting the scalp area image to a Convolutional Neural Network model, and outputting a second feature map; inputting the second feature map to a Transformer model, and outputting a third feature map; and classifying based on the third feature map, and outputting a rating, wherein the rating is to determine the severity of the subject's dandruff.

Preferably, the method for analyzing the severity of the subject's dandruff further has the step of using a scalp tester to take an area of a scalp of the subject to form the scalp area image.

Preferably, the method for analyzing the severity of the subject's dandruff further has the step of compressing and transmitting the second feature map to the Transformer model, wherein a convolution operation is adopted to compress the second feature map.

Other and further features, advantages, and benefits of the invention will become apparent in the following description taken in conjunction with the following drawings. It is to be understood that the foregoing general description and following detailed description are exemplary and explanatory but are not to be restrictive of the invention.

The accompanying drawings are incorporated in and constitute a part of this application and, together with the description, serve to explain the principles of the invention in general terms. Like numerals refer to like parts throughout the disclosure.

BRIEF DESCRIPTION OF THE DRAWINGS

The objects, spirits, and advantages of the preferred embodiments of the present invention will be readily understood by the accompanying drawings and detailed descriptions, wherein.

DETAILED DESCRIPTION OF THE INVENTION

In order to describe in detail the technical content, structural features, achieved objectives and effects of the instant application, the following detailed descriptions are given in conjunction with the drawings and specific embodiments. It should be understood that these embodiments are only used to illustrate the application and not to limit the scope of the instant application.

Figure 1:
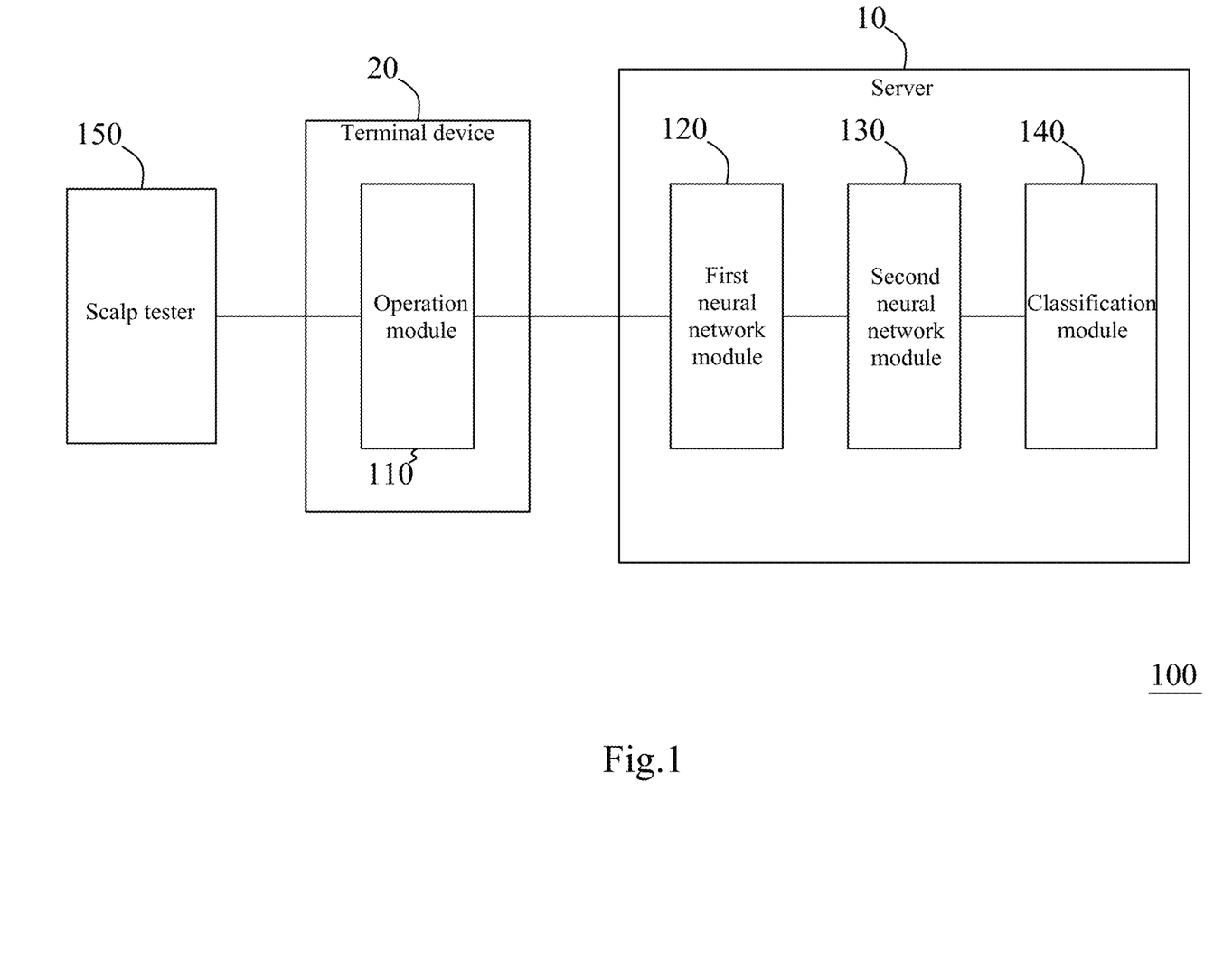
FIG. 1 illustrates a schematic structural view of an embodiment of a smart dandruff analysis system of the present invention.
Figure 2:
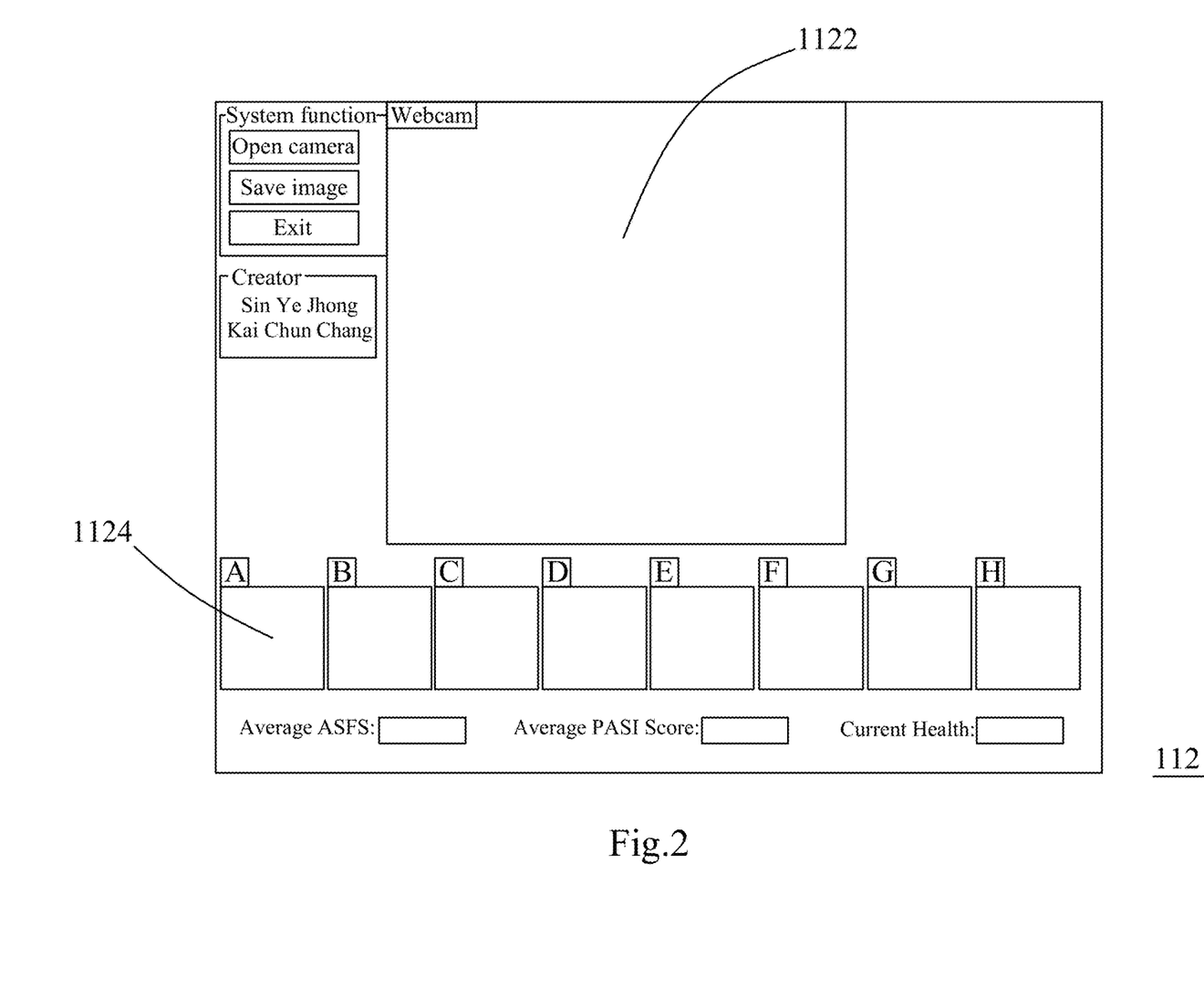
FIG. 2 illustrates a schematic view of an operator interface of an operation module of the present invention.

With reference to FIG. 1, which illustrates a schematic structural view of an embodiment of a smart dandruff analysis system of the present invention. The smart dandruff analysis system 100 includes an operation module 110, a first neural network module 120, a second neural network module 130, and a classification module 140. The operation module is disposed on a terminal device 20, which is as desktop computer, laptop computer, tablet computer, smartphone, etc. The first neural network module 120, the second neural network module 130, and the classification module 140 are disposed on at least one server 10 such as cloud. The server 10 and the terminal device 20 are connected with each other via networks. The operation module 110 provides an operator interface 112 for analyzing scalp, as shown in FIG. 2. The terminal device 20 connects with a scalp tester 150, which takes an area of a scalp of a subject to form a scalp area image, wherein the scalp tester 150 is a digital microscope, model of DMC-1213, that is made by VAST Technologies INC. In addition, there are other options to be instead of aforesaid model.

Figure 4:
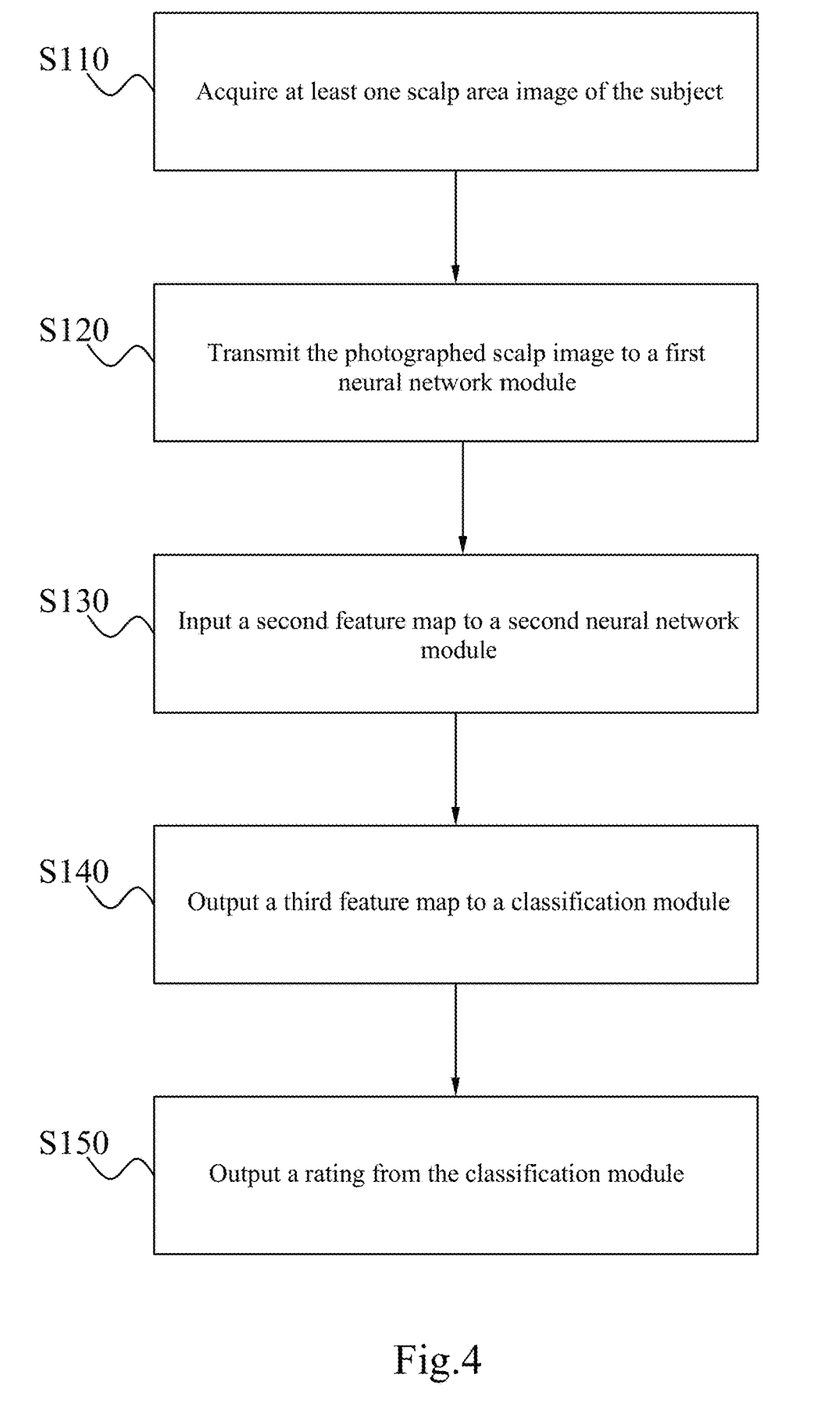
FIG. 4 illustrates a flow chart of a method for analyzing a severity of a subject's dandruff of the present invention.
Figure 6:
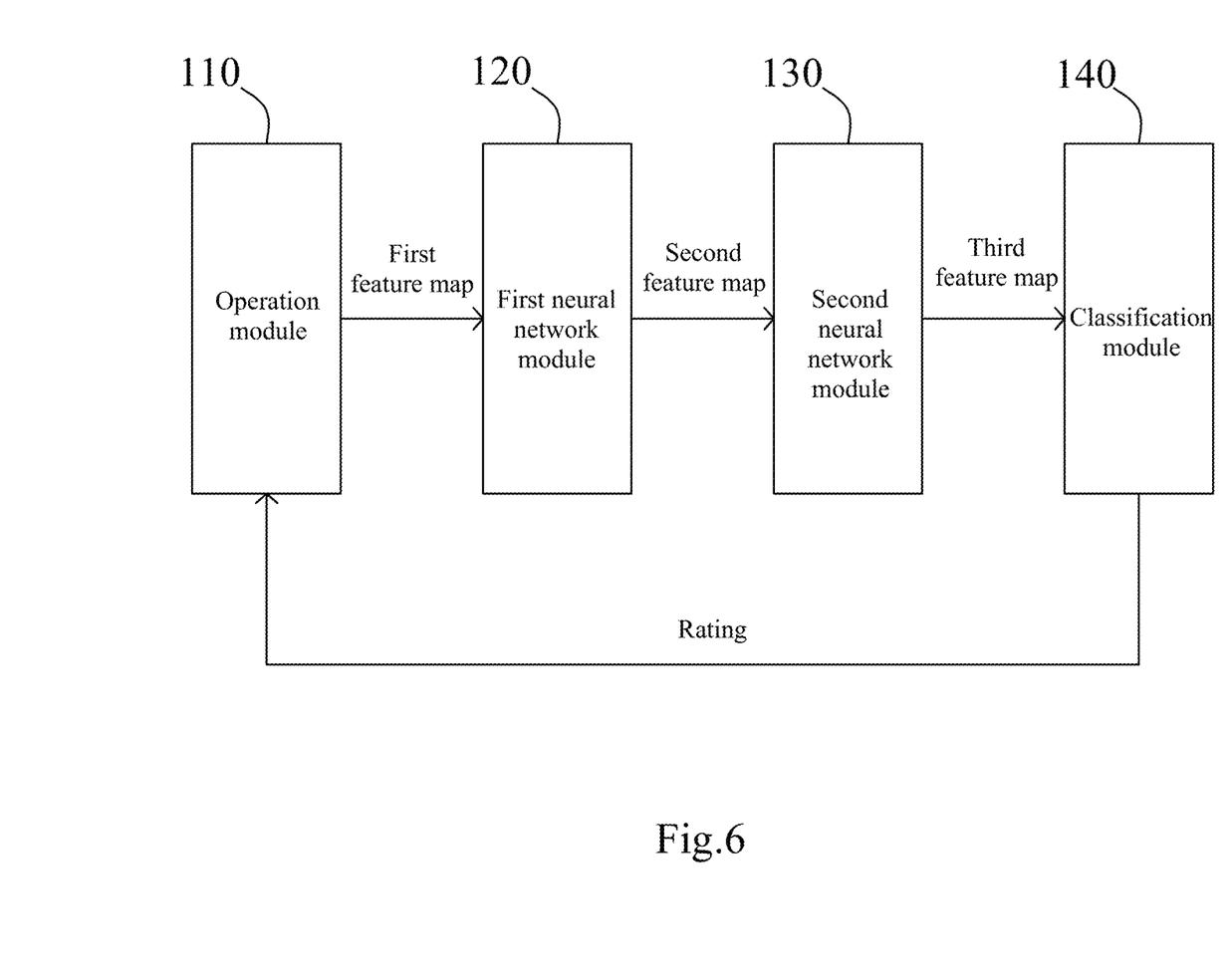
FIG. 6 illustrates a schematic view of an information flow of the smart dandruff analysis system of the present invention.

Referring to FIG. 1, FIG. 4 and FIG. 6, FIG. 4 illustrates a flow chart of a method for analyzing a severity of a subject's dandruff of the present invention, and FIG. 6 illustrates a schematic view of an information flow of the smart dandruff analysis system of the present invention. Step (S110) of the method is to acquire at least one scalp area image of the subject. For the embodiment, eight scalp area images are taken, and the detailed descriptions are as following.

Figure 3:
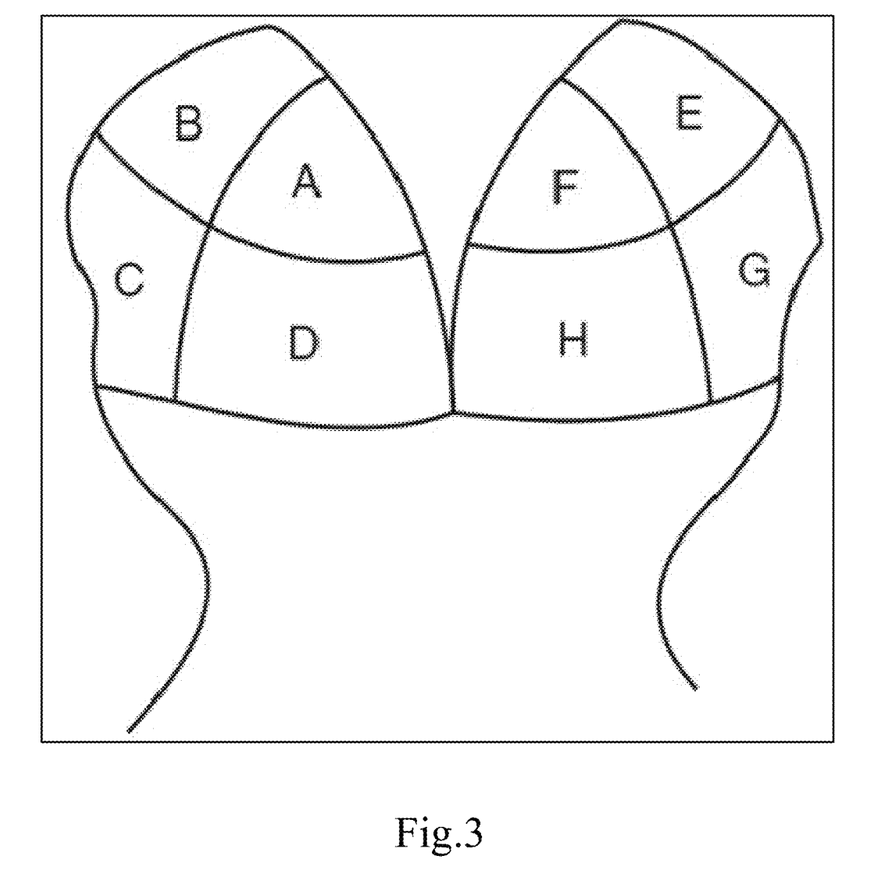
FIG. 3 illustrates a schematic segmentation view of an area of a scalp of the subject of the present invention.

Referring to FIG. 2 and FIG. 3, which illustrate a schematic view of the operator interface of the operation module of the present invention and a schematic segmentation view of an area of a scalp of the subject of the present invention. As shown in FIG. 3, the area of the scalp of the subject is divided into eight areas, such as from area A to Area H. The divided scalp area is based on the paper of "Assessing therapeutic effectiveness of scalp treatments for dandruff and seborrheic dermatitis, part 1: a reliable and relevant method based on the adherent scalp flaking score (ASFS)". Further, such division way, as shown in FIG. 3, may not be limited thereto. The appeared scalp image from the scalp tester 150 is simultaneously shown on a scalp display area 1122 of the operator interface 112, as shown in FIG. 2. If everything is ready, the eight divided scalp areas may be photographed, and thus the photographed eight scalp images are shown on eight scalp image areas 1124 individually.

Based on FIG. 1 and FIG. 4, step (S120) is to transmit the photographed scalp images from the operation module 110 to the first neural network module 120. In detail, the operation module 110 transforms the photographed eight scalp images into vectors, called a first feature map hereinafter, then the eight transformed scalp images are delivered to the first neural network module 120 via networks. In fact, the first neural network module 120 a Convolutional Neural Network (CNN) model, which is constructed by Convolution Layers. Filters are to sieve out features in Convolution Layers, so as to enhance the features which are needed, and weaken or eliminate unwanted features. For example, the subject's scalp may not only have dandruff, but also other features, such as hair, redness, wounds, or spots caused by bacterial infections. The smart dandruff analysis system 100 functions to determine the severity of the subject's dandruff, thus the filter can strengthen the characteristic of dandruff and weaken the other scalp characteristics of the subject.

The Convolutional Neural Network (CNN) model is a Normalizer-Free ResNets model from the paper of "High-Performance Large-Scale Image Recognition Without Normalization", VGGNet, ResNet, EfficientNet, MobileNet, etc.

For other embodiments, the first neural network module 120 further has at least one Pooling Layer, in order to reduce the number of parameters for avoiding a situation of overfitting and achieving anti-noise effect. Besides, since outputted information, called a second feature map hereinafter, from the first neural network module 120 is directly transmitted to the second neural network module 130, the first neural network module 120 is different from general Convolutional Neural Networks. Therefore, the first neural network module 120 may not have a Fully Connected Layer.

Step (S130) is to input the second feature map to the second neural network module 130 that connects with the first neural network module 120. The second neural network module 130 is a Transformer model. The Transformer model was proposed by Google in the paper of "Attention Is All You Need" in 2017. The issues of the second neural network module 130 being a Transformer model, and if it is the Convolutional Neural Network (CNN) model, what is the differences, they will be described in detail as following.

Figure 5A:
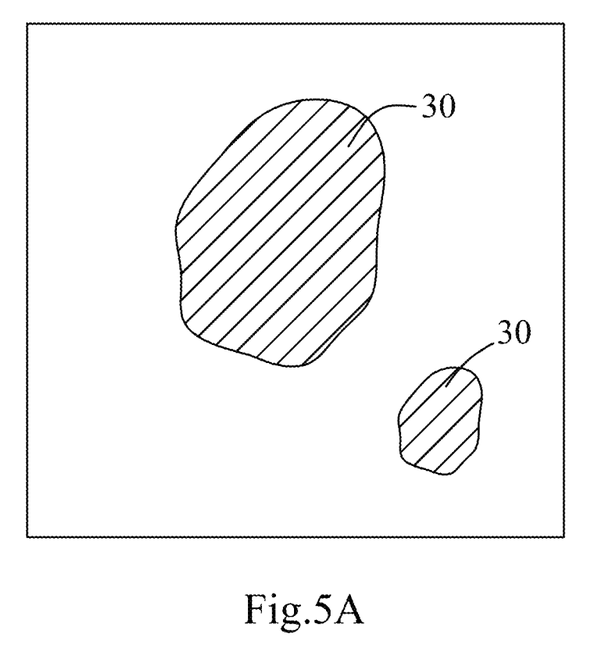
FIG. 5A and FIG. 5B illustrate schematic views of dandruff distributed on the scalp of the subject of the present invention.
Figure 5B:
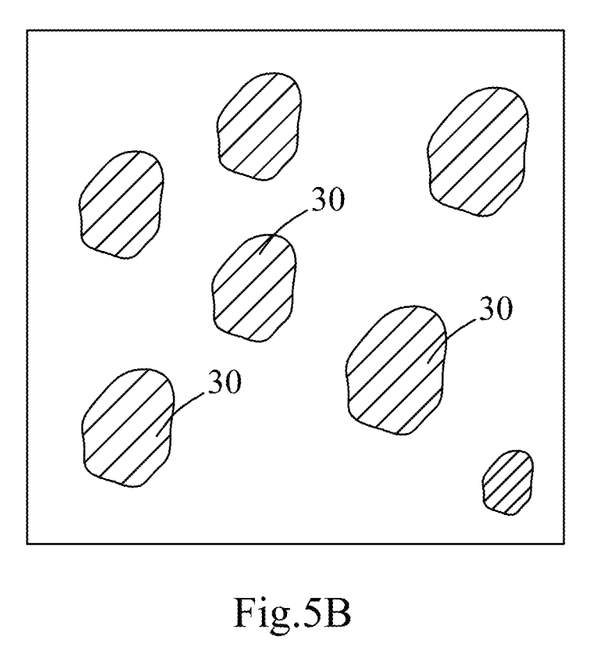

With respect to FIG. 5A and FIG. 5B, which illustrate schematic views of dandruff distributed on the scalp of the subject of the present invention. According to FIG. 5A, the dandruff distribution is slightly limited in a certain area, but FIG. 5B does not going the same way. Depending on the characteristics itself, the Convolutional Neural Network (CNN) model can feel partial characteristics more than other models, and the relativity of two areas with longer distance may not be involved. In other words, the receptive field of the Convolutional Neural Network (CNN) model is smaller. Therefore, even if the amount of the dandruff 30 in FIG. 5B is more than FIG. 5A's, the Convolutional Neural Network (CNN) model may still judge the situation in FIG. 5A is worse. On the contrary, The Transformer model applies a self-attention means to focus on the relatives of two areas with longer distance. That is, the receptive field of the Transformer model is larger, so as to preferably and correctly determine the dandruff distribution, as shown in FIG. 5B.

For the embodiment, the Transformer model adopts a Vision Transformer model that is from the paper of "AN IMAGE IS WORTH 16×16 WORDS: TRANSFORMERS FOR IMAGE RECOGNITION AT SCALE". But that is not limited thereto, and Transformer model could be CaiT, LV-ViT, BEiT, etc.

After the second feature map is transformed to a third feature map by the second neural network module 130, a following step is step (S140), which is to output the third feature map to the classification module 140. To the embodiment, the classification module 140 is constructed by two Fully Connected Layers. Step (S150) is to output a rating from the classification module 140 after receiving and calculating the third feature map. In the embodiment, references for six ratings are from the paper of ASFS and the inventor of the instant application sets/designs six conditions for the six ratings. The six ratings and their corresponding conditions are listed below:

(1) Zero point: No dandruff;
(2) Two points: Finely crushed dandruff (small desquamation, small pieces);
(3) Four points: Flaky dandruff (small desquamation, flakes);

(4) Six points: Lumpy dandruff (moderate desquamation, lumpy);
(5) Eight points: Massive dandruff (moderate desquamation, lumpy); and
(6) Ten points: Massive dandruff (thick desquamation, clumpy).

Figure 7:
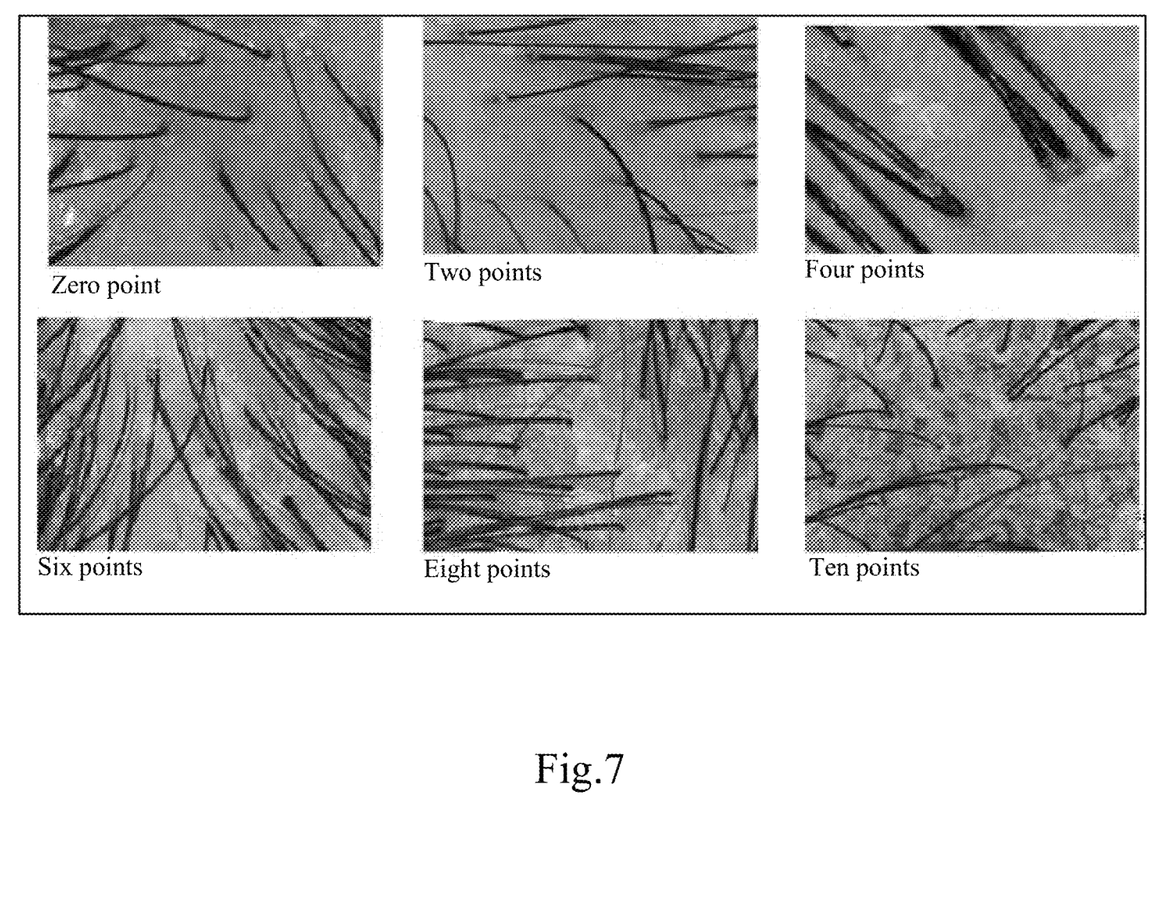
FIG. 7 illustrates schematic views of real dandruff conditions corresponding to various ratings.

As shown in FIG. 7, which illustrate schematic views of real dandruff conditions corresponding to various ratings. The ratings are variable and not limited thereto. After the classification module 140 outputs the rating, the rating is transmitted to the operation module 110 and displayed on the operator interface 112. Based on the embodiment, the smart dandruff analysis system 100 rates the scalp areas of the eight subjects. However, those persons skilled in the art should be able to understand that it is possible to use summation or weighting to make comprehensive ratings on the subjects' entire scalp as well. When receiving the ratings, the staffs provide improvement plans corresponding to the subjects to improve their dandruff problems.

Figure 8:
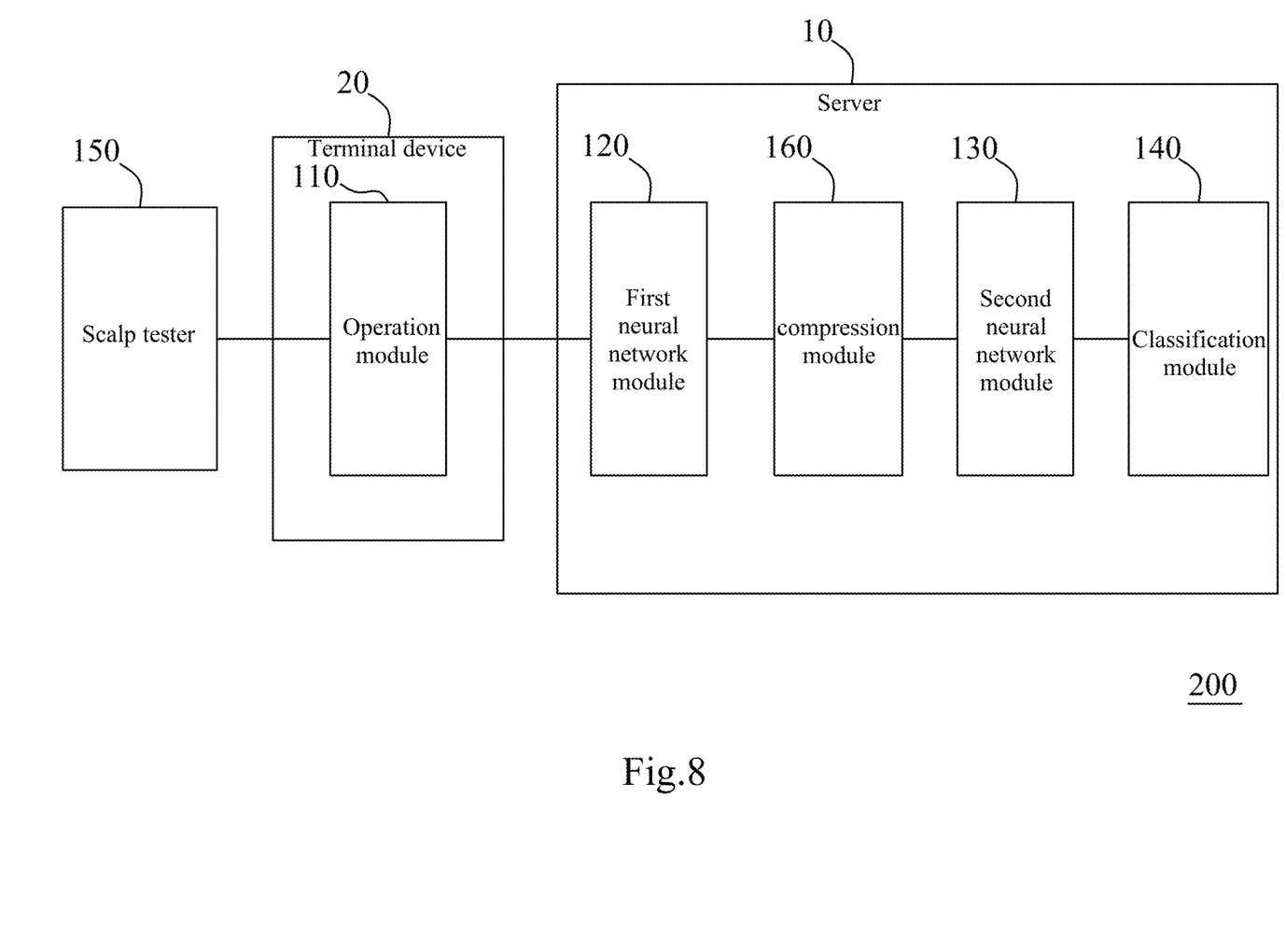
FIG. 8 illustrates a schematic structural view of another embodiment of the smart dandruff analysis system of the present invention.

With reference to FIG. 8, which illustrates a schematic structural view of another embodiment of the smart dandruff analysis system of the present invention. Compared with the smart dandruff analysis system 100, a smart dandruff analysis system 200 further has a compression module 160, which is connected between the first neural network module 120 and the second neural network module 130, and receives and compresses the second feature map from the first neural network module 120, then transmits the compressed second feature map to the second neural network module 130. That is to say, after the Convolutional Neural Network (CNN) model outputs the second feature map, the second feature map is compressed and transmitted the Transformer model.

According to the second embodiment, the compression module 160 compresses the second feature map by means of a convolution operation. For example, the second feature map before compression is a three-dimensional array of [N×N×M], wherein M is greater than 3. Performing the convolution operation on the three-dimensional array of [N×N×M] and a three-dimensional array of [1×1×3] is to obtain the three-dimensional array of [N×N×3], which is the second feature map after compression. Depending on aforesaid operation, the whole operation is simpler, and the first neural network module 120 and the second neural network module 130 are effectively connected with each other in series, so as to achieve more stable identification, determination, etc.

For the embodiment, the smart dandruff analysis system 100 adopts a Semi-supervised Learning when training, since the professional operators who know this art are rare and with higher pay. Therefore, a Supervised Learning may highly raise up cost. In detail, the embodiment adopts a FixMatch algorithm, from the paper of "Simplifying Semi-Supervised Learning with Consistency and Confidence to execute the Semi-supervised Learning". Same theory, not only the present invention uses the Semi-supervised Learning, but also other learnings do.

Besides, each of the scalp area image uploaded by every one of the terminal devices 20 can be a further training reference of the smart dandruff analysis system 100, so as to improve the precision of the system.

As aforesaid, the smart dandruff analysis system 100 has the following advantages:
(1) Rating the scalp of the subject by way of artificial intelligence (AI) may bring up those operators who have not been trained professionally, so as to decrease cost as well.
(2) Combining the Convolutional Neural Network (CNN) model with the transformer model increases the accuracy of the rating.
(3) The operation module is disposed at the terminal devices for AI operations. Namely, the first neural network module, the second neural network module and the classification module are disposed in the Cloud. Therefore, as soon as the partial for the AI operations is updated, all of the terminal devices are renewed as well.

Although the invention has been disclosed and illustrated with reference to particular embodiments, the principles involved are susceptible for use in numerous other embodiments that will be apparent to persons skilled in the art. This invention is, therefore, to be limited only as indicated by the scope of the appended claims

What is claimed is:

1. A smart dandruff analysis system for analyzing a severity of a subject's dandruff, comprising:
   an operation module, receiving a scalp area image of the subject and transforming the scalp area image into a first feature map;
   a first neural network module, a Convolutional Neural Network (CNN) model, electrically connecting with the operation module in order to receive the scalp area image and transform the scalp area image into a second feature map;
   a compression module, which is connected first neural network module, receiving and compressing the second feature map;
   a second neural network module, a Transformer model, electrically connecting with the compression module in order to receive the compressed second feature map and transform the compressed second feature map into a third feature map; and
   a classification module, electrically connecting with the second neural network module in order to receive the third feature map and output a rating;
   wherein the rating is to determine the severity of the subject's dandruff.

2. The smart dandruff analysis system according to claim 1, further comprising a scalp tester, which takes an area of a scalp of the subject to form the scalp area image.

3. The smart dandruff analysis system according to claim 2, wherein the scalp tester is a digital microscope.

4. The smart dandruff analysis system according to claim 1, wherein a Semi-supervised Learning is adopted when training.

5. The smart dandruff analysis system according to claim 1, wherein the operation module is disposed on at least one terminal device, and the first neural network module, the second neural network module and the classification module are disposed on at least one server.

6. A method for analyzing a severity of a subject's dandruff comprising the steps of:
   (a) acquiring at least one scalp area image of the subject, and transforming the scalp area image into a first feature map;
   (b) inputting the scalp area image to a Convolutional Neural Network model, and outputting a second feature map;
   (c) compressing and transmitting the second feature map to the Transformer model using a convolution operation;
   (d) inputting the compressed second feature map to a Transformer model, and outputting a third feature map; and (e) classifying based on the third feature map, and outputting a rating, wherein the rating is to determine the severity of the subject's dandruff.

7. The method for analyzing the severity of the subject's dandruff according to claim 6 further comprising the step of: using a scalp tester to take an area of a scalp of the subject to form the scalp area image.

\* \* \* \* \*